United States Patent [19]

Hadden

[11] 4,266,423
[45] May 12, 1981

[54] USE OF ACID AS AN ANALYSIS AID IN SALTED MEAT SAMPLES

[75] Inventor: James P. Hadden, Tipp City, Ohio
[73] Assignee: Hobart Corporation, Troy, Ohio
[21] Appl. No.: 80,841
[22] Filed: Oct. 1, 1979
[51] Int. Cl.³ .............................................. G01N 5/04
[52] U.S. Cl. ................................. 73/15 B; 23/230 PC
[58] Field of Search .............. 73/15 B, 76; 23/230 PC

[56] References Cited

U.S. PATENT DOCUMENTS

| | | | |
|---|---|---|---|
| 3,178,929 | 4/1965 | Gross | 73/76 |
| 3,890,825 | 6/1975 | Davis | 73/15 |
| 3,916,670 | 11/1975 | Davis et al. | 73/15 B |

*Primary Examiner*—Herbert Goldstein
*Attorney, Agent, or Firm*—Biebel, French & Nauman

[57] ABSTRACT

The accurate determination of the fat, moisture, and protein content of salt added meats by means of thermal extraction is complicated by the enhanced fat and moisture binding capability that salt gives to meat proteins. This effect is counteracted by the addition of a controlled amount of acid to a salted meat sample which lowers the pH of the meat proteins below their isoelectric points. In a preferred embodiment, citric acid is mixed with a salted meat sample and the sample is then exposed to microwave energy for a time sufficient to achieve a relatively constant chemical analysis in the residue which is related to the amount of fat and moisture rendered from the sample.

8 Claims, 5 Drawing Figures

U.S. Patent May 12, 1981 Sheet 2 of 2 4,266,423
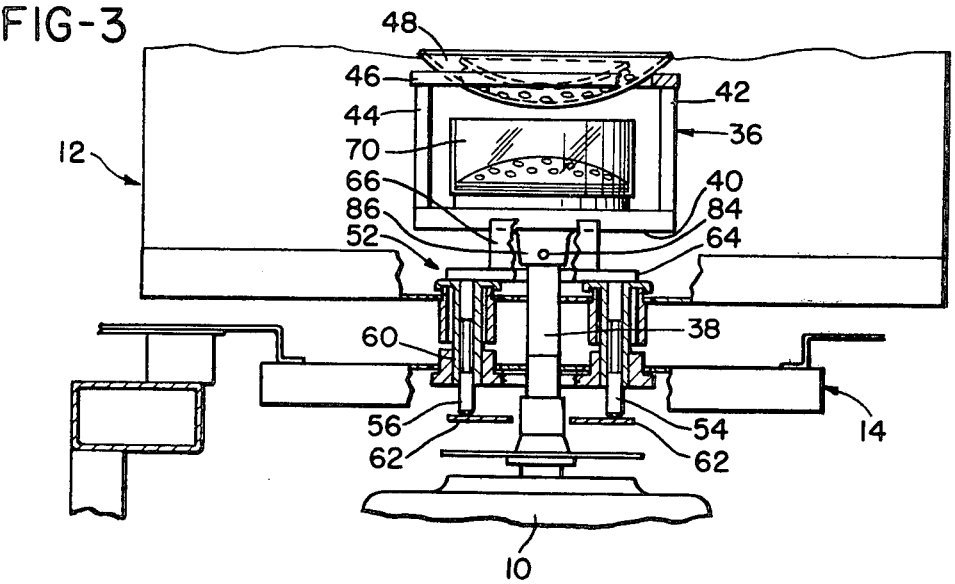
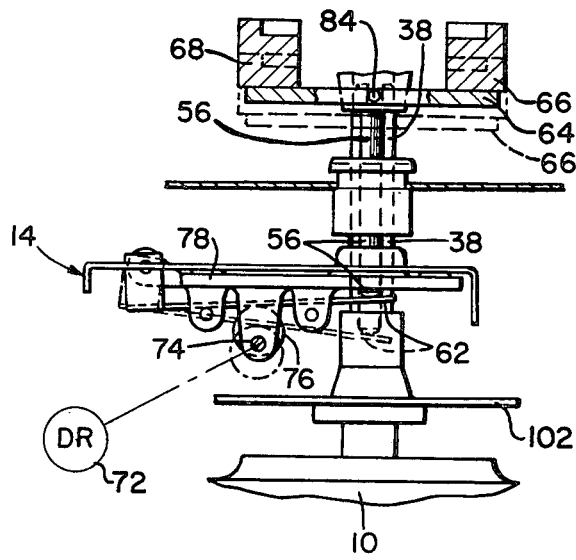
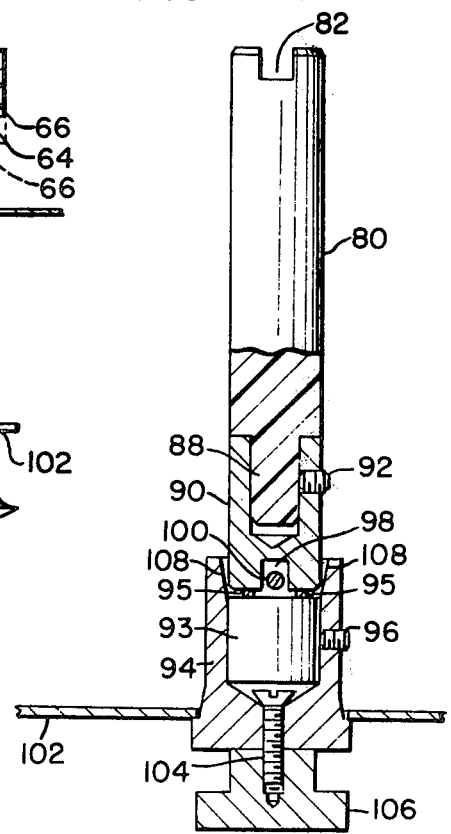

USE OF ACID AS AN ANALYSIS AID IN SALTED MEAT SAMPLES

BACKGROUND OF THE INVENTION

This invention relates to a method of determining, by means of thermal extraction, the fat, moisture, and protein content of meat samples, and more particularly to a method of analyzing salted meat samples to which acid has been added. This application is related to copending application Ser. No. 080,802, filed Oct. 1, 1979, entitled "Method and Apparatus for Analysis of Meat Products" and Ser. No. 080,803, filed Oct. 1, 1979 entitled "Magnetic Coupling for a Weighing Balance Assembly," both filed on even date herewith and assigned to the assignee of the present invention.

In meat products which are intended for human consumption and which are comminuted during processing, the problems of accurate control of fat and/or moisture content arises. Typical of such meat products are ground beef, pork, veal and lamb, pork sausage, and blended meat products such as bologna, weiners, and liverwurst. In preparing these products, the usual procedure is to feed chunk meat into a grinder and then into a mixer where the meat and fat portions of the product are blended together.

Meat protein, as do many food proteins, has the ability to combine with fats to form a solid emulsion. That is, the protein will bind with fats to form a physically and chemically stable matrix. This phenomenon is a necessary element in the production of many important food products such as salad dressings, mayonnaise, bologna, and weiners. There are several important variables which affect the stability and strength of such emulsions. Among these are the temperature at which the emulsion is formed, the amount of work (mixing) done in blending the components, and the presence of one or more emulsifying agents.

In the production of blended meat products such as bologna, salt is added to the meat as an emulsifying aid which solubilizes the protein in the meat and allows it to encapsulate the fat particles. This results in a more stable product, and this stability persists even upon exposure of the product to thermal energy (i.e., heating or cooking).

The temperature at which the emulsion is formed also has some effect on its stability. For example, in the production of a beef and pork bologna, it has been found that a more stable product is produced if it is initially comminuted at a temperature between 50° and 60° F. A product formed, for example, at 40° F. will exhibit small pockets of separated fat and gelatin (protein) during cooking and will lose a greater percentage of its overall fat and moisture during heating than a product which was initially formed at 50°-60° F.

Likewise, the amount of work (mixing) performed on a blended meat product will have an effect on the stability of the emulsion which is formed. Not unexpectedly, for typical processing operation the greater the amount of work performed in forming the product, the more stable the emulsion which is formed.

As can be seen, several factors can affect the respective amounts of fat and moisture a meat sample will lose during heating. In meat analysis processes which utilize heat to vaporize moisture and render fat as a liquid from a sample such as the processes disclosued in Davis et al, U.S. Pat. No. No. 3,916,670, and in the above-mentioned related copending applications, all of the above-discussed factors will affect the results obtained and make accurate calibration impossible. Although the amount of work performed on a sample and the temperature at which it is prepared can be controlled for fresh meat samples, the addition of varying amounts of salt to blended meats substantially increases the fat binding capabilities of the meat proteins. Thermal energy alone will not overcome this effect. As can be seen, the need exists in the art for a method of analysis in which the physical and chemical state of a salted meat sample to be analyzed can be controlled so that fast, accurate, and reproducible results can be obtained on a variety of meat samples.

SUMMARY OF THE INVENTION

The present invention meets this need by the addition of a controlled amount of acid to a salted meat sample. The addition of acid to a meat sample lowers the pH of the sample below the isoelectric point of the proteins contained in the sample. Below the isoelectric point of a meat protein, the functional groups on the protein are less able to bind fat and moisture. Thus, the addition of acid counteracts the effects of added salt to the meat sample and permits more accurate calibration of constants to be used in meat analysis procedures.

The preferred acid for use in the invention is citric acid although any acid will have the requisite pH lowering effect on a meat sample. Citric acid is commercially available as a food grade acid and presents no special handling problems when used in a meat processing facility. Additionally, citric acid is available in a preferred encapsulated form which can be mixed with a meat sample. The encapsulation melts at 145°-150° F. during heating of the sample for analysis permitting precise control of when the desirable pH lowering effect of the acid is activated.

In a preferred embodiment, the process of the present invention is used in conjunction with the meat analyzer disclosed in application Ser. No. 080,802, entitled "Method and Apparatus for Analysis of Meat Products" and filed on even date herewith. The meat analyzer comprises in combination a weighing balance assembly and a microwave oven. The weighing platform of the balance assembly extends into the oven and is adapted to receive a 70-80 gram sample of meat for analysis. The sample is first weighed and then exposed to microwave energy which releases moisture as water vapor and fat as a liquid. The fat rendered from the meat is collected off of the balance assembly while the weight loss in the sample is constantly monitored during the heating cycle. When the rate of weight loss drops below a predetermined value, heating is terminated, and the sample residue and fat are cooled and weighed. By measuring the amount of fat and moisture lost from the sample during heating, correlated values of total moisture, fat, and protein content are derived.

When a salted meat blend is analyzed, a 70-80 gram sample is weighed and then removed from the analyzer where it is mixed for 30 seconds in a chilled bowl with an acid. The temperature of the sample is maintained at between 30° and 50° F. In a preferred embodiment, approximately 3 grams of an encapsulated food grade citric acid is mixed with the sample, and the sample is returned to the meat analyzer. During the heating cycle, the encapsulation around the acid melts away and the acid lowers the pH of the sample to below the isoelectric point of the proteins therein causing a decrease in the fat binding ability of those proteins. The use of acid permits precise control of the condition of salted meat samples and, thus, permits accurate calibration of the meat analyzer.

Accordingly, it is an object of the present invention to control the physical and chemical state of salted meat samples so that accurate analyses of the fat, protein, and moisture content of such meats can be made. This and other objects and advantages of the invention will become apparent from the following description, the accompanying drawings, and the appended claims.

BRIEF DESCRIPTION OF THE DRAWINGS

FIG. 3 is a view of the portion of the apparatus shown in FIG. 2, with the various elements shown in their respective positions after cooking has been terminated;

FIG. 4 is a side view of the mechanism which raises and lowers the dish support assembly; and FIG. 5 is a detailed sectional view of the magnetic coupling of the stem of the weighing balance to the base thereof.

DESCRIPTION OF THE PREFERRED EMBODIMENTS

Figure 1:
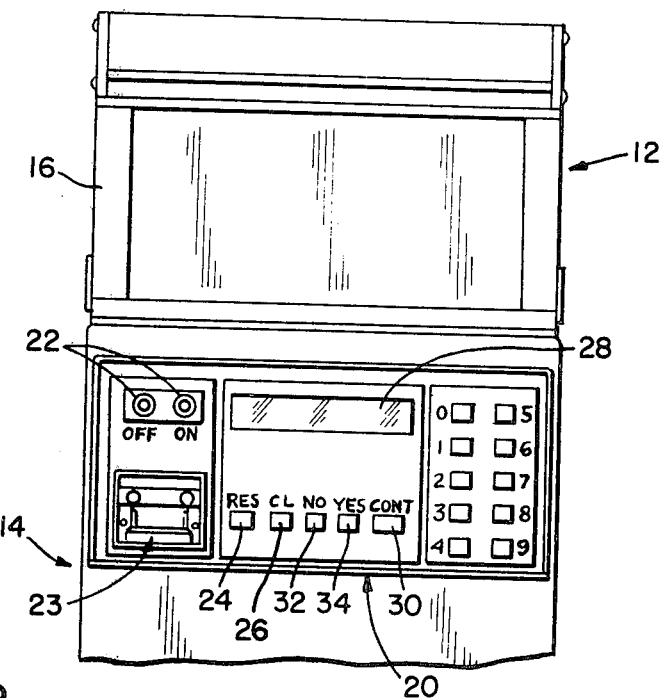
FIG. 1 is a front view of the apparatus of the present invention illustrating the control panel and microwave oven.

Although the present invention will be described in terms of its use in a specific meat analyzer system, it will be apparent to those skilled in the art that the process of the present invention is broadly applicable to the thermal extraction analysis of salted meats for their fat, moisture, and protein contents.

Analysis of food material, such as prepared samples of a meat product, is provided by rendering or "cooking" the sample to release from it moisture, primarily in the form of vapor, and fat, primarily as liquid which is collected separately from the solid residue and removed from the scale to avoid fluctuations in weight readings. By weighing the sample before and after cooking, and both with and separate from the fat, it is possible to calculate percentage of moisture and percentage of fat. Having reference to certain formulae which are well known in the meat industry, it is possible to calculate the percentage of protein in meat.

In a preferred embodiment, a comminuted meat sample is selected such that the sample weight is in the range of 70 to 80 grams. The reason for this is that the "cooking" cycle may be maintained short, e.g., 2 to $4\frac{1}{2}$ minutes. The term "cooking" in accordance with this invention is meat heated short of charring but far too well cooked to be edible in the normal sense. The use of microwave energy offers the singular advantage of generating heat throughout the sample so that it is uniformly and evenly heated. The energy from the source penetrates the sample causing oscillation of dipolar molecules, such as water, which attempt to align themselves with the polarity of the electromagnetic field, and thereby generate heat uniformly throughout the sample. The moisture, or water is vaporized and released directly as vapor. The fat molecules are excited sufficiently by the microwave energy to cause melting of the fat which then drips from the sample into a collection dish. By heating the sample short of charring, decomposition of substantial amounts of protein and fat is avoided even though some fat, moisture, and protein remains in the solid residue.

The microwave cooking thus does not remove all of the fat or moisture, but this has been found not to be critical to the determination of the percentages of these components as taught in above-mentioned U.S. Pat. Nos. 3,890,825 and 3,916,670. It has also been observed that some of the protein is removed with the moisture by decomposition and vaporization. These factors are compensated for by generating a set of constants which are a function of oven design, i.e., spacing between the microwave energy source and sample, intensity of energy source, and rate of heating and type of meat. Also a factor is the loss of fat, protein, etc., due to spattering and the vaporization of some of these components. Thus, any microwave oven will have a set of constants which can be calculated, the constants being determined easily by a simple calibration procedure, and being valid for each oven of the same design, although it may vary from one design of oven to the next. The procedure for developing such constants is discussed in the above-mentioned patents and is incorporated herein by reference. Those sampling techniques and use of multiple regression analysis have been extended to include the determination of constants for salt content and temperature in the present invention.

In general, the analysis system operates as follows. The sample holder assembly, sample holder, and sample holder cover are first weighed to establish an initial tare weight which is then stored. The fat collection dish is then lowered onto the sample holder assembly and weighed to establish a second combined tare weight which is stored. (It should be understood that whenever "collection dish" is mentioned, this also includes a dish paper and watchglass which are contained in the collection dish and help to prevent spattering.) The collection dish is then raised off of the sample holder assembly in preparation for the cooking cycle. A prepared sample of meat is then placed in the sample holder, covered, and loaded onto the sample holder assembly. After measuring and storing the weight of the sample plus the initial tare weight, the cooking cycle is initiated and continued until the rate of weight loss of the sample falls below a predetermined value. During the cooking cycle, the fat collection dish is maintained off the sample holder assembly so that the rendered fat it collects does not cause any fluctuations in weight readings. At the end of the cooking cycle, the oven is shut off and the fat containing collection dish is lowered into the sample holder assembly where the combined weight of the sample holder assembly, sample holder, sample holder cover, collection dish, sample residue, and rendered fat is recorded. The residue is then removed from the balance and the combined weight of the sample holder assembly, sample holder, sample holder cover, collection dish, and rendered fat is recorded. The moisture, fat, and protein content of the sample may then be calculated using equations which will be set forth below.

As is understood, these calculations may be automatically carried out by a computer which functions with the balance assembly in a conventional manner.

It will be apparent to those skilled in the art that the present system may be used to determine only fat content in contrast to determination of each of moisture, fat, and protein, or may be used to determine only moisture. If used to determine only protein, this can be done by determining fat and moisture but reporting only the protein results.

Various types of electronic means known to a person skilled in the art may be used to perform the weighing and calculating functions previously described. For example, a number of commercially available balances provide digital output of weight information which is easily processed in a small general purpose or special purpose computer. With such equipment the calculations are carried out manually or under the control of a set of instructions programmed into the computer.

It has been discovered that a more nearly automatic system can be provided wherein the weighing, recording, and cooking operations are performed in a fairly rapid manner, and with minimum attention which can be provided by relatively unskilled labor. This system also provides certain additional manufacturing advantages since it minimizes the need to standardize each type of oven used. The system also provides both an automatic visual readout of percentages of moisture, fat, and protein, and a printout of this information.

Figure 2:
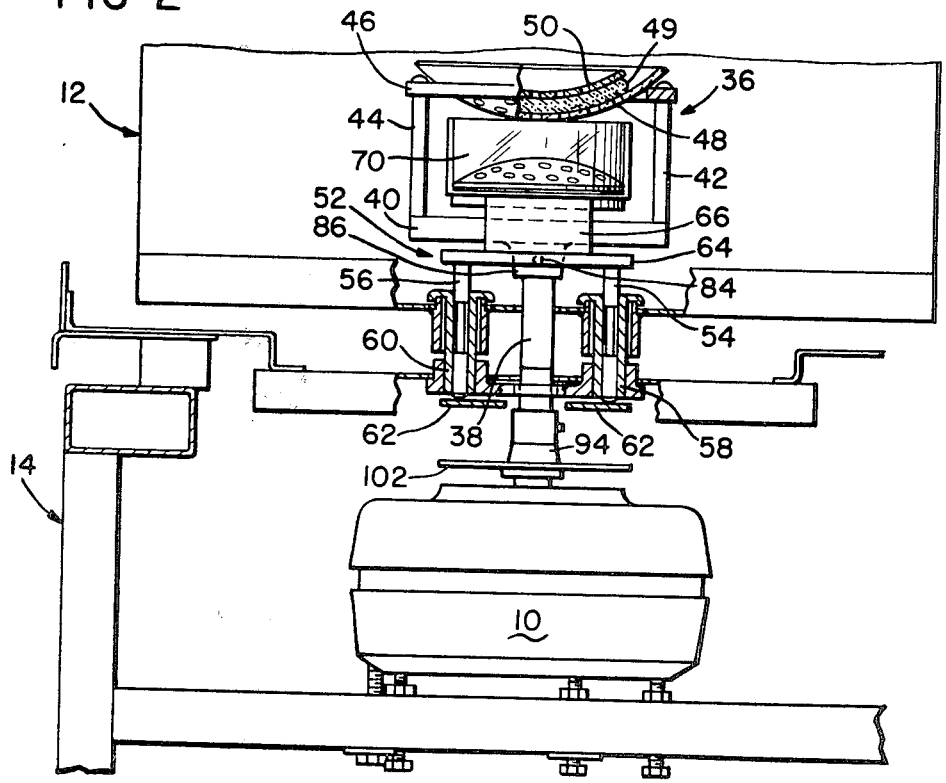
FIG. 2 is a view of the weighing apparatus, sample holder assembly, and fat collecting dish and dish support assembly in their respective positions during the cooking of the sample.

Referring now to FIGS. 1 and 2, this automated system includes a weighing balance assembly 10 incorporated beneath a microwave oven 12 which is supported on a suitable cabinet 14. The oven is a standard type of microwave oven using a magnetron with a frequency of 2450 megahertz, although frequencies of between 900 to 2500 megahertz may be used. This oven may be basically the same as a Model M312 microwave oven commercially available from the Hobart Corporation.

Oven 12 includes a hinged door 16. Below the oven on cabinet 14 is a control panel 20 which includes a master power (ON-OFF) switch 22 as well as the following controls. RESET switch 24 interrupts the program and returns control to the start of the program. CLEAR switch 26 clears any digits displayed in a window 28. CONT switch 30 when touched indicates that a command has been completed and continues the program to the next command. By touching switches NO 32 or YES 34 an operator can answer questions displayed in window 28. Finally, numbers entered into the program by touching digit switches 0-9 will be displayed in the window 28. A printer 23 records and displays information on a paper ticket.

The weighing balance assembly 10 includes a precision balance such as a modified Model 5300 top loading balance commercially available from the Voland Corporation of New Rochelle, N.Y., having a sample holder assembly 36 mounted within the oven cavity on the pedestal stem 38 of the balance. As best illustrated in FIG. 5, the upper portion 80 of stem 38 is fabricated of a plastic, such as polypropylene, or other material substantially unaffected by microwave energy. At the upper tip of stem 38 is a slot 82 which is adapted to straddle pin 84 in boss 86 (illustrated in FIGS. 2 and 3) to provide proper alignment of the sample holder assembly 36 in the system.

The opposite tip 88 of upper portion 80 of the stem is adapted to fit into a hole bored in lower portion 90 of stem 38 and is held therein by suitable means such as set screw 92. Lower portion 90 of stem 38 is fabricated of a ferromagnetic material and is magnetically coupled to magnet 93 having poles 95 and seated in holder 94. A suitable magnet for use in the device has been found to be a BM-1908×¾ magnet commercially available from Bunting Magnetics Co., Elk Grove Village, Ill. The magnet is held in place by suitable means such as a set screw 96. Stem 38 is maintained in proper alignment in holder 94 by means of slot 98 which straddles pin 100. A disc-like shield 102 protects the weighing mechanism from any possible fat drippings which may inadvertently escape from the oven. Holder 94 is secured by suitable means such as screw 104 to the balance mechanism 106.

As shown in FIG. 5, the upper portion 108 of the inner wall of holder 94 flares outwardly at an angle of about 7.5° from vertical to permit stem 38 to rock slightly away from the vertical while in the holder. The vertical movement of the stem is limited by the clearance between the stem and a ¼ wavelength choke seal which substantially eliminates any leakage of microwave energy from the opening in the oven bottom wall. Typically, this clearance is about ¼ inch. Thus, the magnetic coupling normally maintains the stem in a desired vertical position while still permitting a slight rocking motion of the stem relative to the magnet. This rocking motion, without magnetically uncoupling the stem, avoids the problem of transmitting possibly damaging forces or torques to the internal mechanism of the weighing device. The attraction between the magnet and the metallic lower portion of the stem insures that the stem will return to vertical once any external forces such as bumping or jarring have been removed from the stem and sample holder assembly.

Although a weighing balance having the weighing platform separated from the body portion by an elongated single shaft force transmitting element as does the Voland device is preferable for the present apparatus, it is possible to employ other forms of weighing apparatus including balances of the type wherein the force transducer is located inside the microwave oven cavity and only electrical wires are conducted to the cavity exterior if suitable changes are made in the apparatus. Balances which are totally mounted in the oven cavity and conduct electrical signals to the exterior would for example require suitable shielding and filtering devices to protect the balance transducers from microwave heating and to prevent microwave radiation from being conducted to the exterior of the heating cavity by the balance signal wiring.

Sample holder assembly 36 includes a base member 40 having a suitable connecting means such as boss 86 and pin 84 for releasably attaching the assembly to stem 38 of the balance. Boss 86 consists of a hollow shaft which fits over stem 38 and contains an alignment pin 84 to properly align the assembly on the stem. A pair of upstanding end walls 42 and 44 support an annular disc 46 which is attached thereto. The opening in disc 46 is proportioned to receive a sample holder 48 which may be a perforated watchglass. As illustrated in FIG. 2, a sample 49 of prepared meat is placed on sample holder 48 and is then covered by a sample holder cover 50. Preferably, sample holder cover 50 is also perforated to permit the escape of moisture from the sample as vapor during the cooking cycle. Both holder 48 and cover 50 may be formed of Pyrex glass or polytetrafluoroethylene (Teflon, a trademark of the duPont Company) or other suitable material which is nonresponsive (i.e., not heated) or only mildly responsive to microwave electromagnetic energy.

Also associated with weighing balance assembly 10 is a dish support assembly generally indicated at 52. This assembly includes a pair of vertically extending shafts 54 and 56 which extend through bushings 58 and 60, respectively, and rest on platform 62. Bushings 58 and 60 extend through the base of oven 12 into cabinet 14 and are sealed in the same manner as stem 38 to prevent leakage of microwave energy from the oven during operation. An annular disc-shaped support element 64 is attached to shafts 54 and 56 and surrounds stem 38. It has mounted on opposite sides thereof, a pair of upstanding members 66 and 68 which are adapted to support a dish 70.

Dish support assembly 52 is raised or lowered by raising or lowering platform 62. As best shown in FIG. 4, this is accomplished by a drive means 72 suitably connected to a shaft 74 which turns cam 76. Cam 76 is in direct contact with the underside of platform 62. Rotation of cam 76 causes platform 62, which is hinged at one end to support member 78 which is attached to a portion of cabinet 14, to raise and lower shafts 54 and 56. A limit switch (not shown) cuts off drive means 72 when the upper or lower (shown in dashed lines in FIG. 4) limit of platform movement is achieved.

In this manner, dish 70 is raised off of sample holder assembly 36, as shown in FIG. 2, during the cooking cycle. Fat rendered from the sample during cooking is collected in dish 70 off of the weighing scale, avoiding erratic fluctuations in weight readings caused by explosions and spattering or dripping of the hot fat in the dish. After the cooking cycle has been terminated, dish 70 is lowered onto sample holder assembly 36 as shown in FIG. 3 where it is weighed.

The weighing balance device includes a digital electronic output and a microprocessor-controller as taught in the above-mentioned U.S. Pat. Nos. 3,890,825 and 3,916,670. The microprocessor-controller properly sequences the operation of the device and provides outputs to the display window 28 and printer 23. The operation of the microprocessor-controller is detailed in the above-mentioned patents and is herein incorporated by reference.

To commence operation for fresh meat analysis, the power is turned on by pressing ON switch 22. Then, the date, run number, meat type code, and temperature of the prepared sample are successively entered by the operator alternatively touching the appropriate digit switches and then the CONT switch 30 on the control panel. The microprocessor is programmed to utilize different predetermined values of slopes and intercepts in calculating the final percentages of fat, moisture, and protein in the sample. By entering the coded meat type (i.e., beef=0, pork=1, etc.) the microprocessor utilizes proper values for that particular type of meat for the calculations.

After this preliminary information has been entered, the command "PREPARE OVEN" is displayed in window 28. Then, the operator opens the oven door 16 and loads the sample holder assembly 36 including the sample holder 48 and sample cover 50 onto the weighing balance. At this time, also, collection dish 70 is loaded onto dish support assembly 52 which is in a raised position. After the operator closes the door 16 and touches CONT switch 30, a first tare weight (denoted SPT) of the sample support assembly, holder, and cover is taken and stored. The dish support assembly is then lowered causing dish 70 to be deposited onto the base member 40 of the sample holder assembly and a second tare weight (denoted S&D) which includes the weight of the collection dish is taken and stored. The microprocessor makes a calculation to confirm that the weight value of the collection dish (denoted as DSH) is within predetermined expected limits and that the operator has placed the dish on the dish support assembly. (The weight value DSH is not saved by the microprocessor.) When this check is completed, the microprocessor causes the dish support assembly 52 to be raised so that the dish 70 is off of the sample holder assembly base member 40. Each actuation of the dish support assembly 52 to raise or lower the dish 70 is controlled by the microprocessor through its selective operation of the drive means 72 in a conventional manner.

Once the tare weights are recorded, the dish weight check performed, and the dish 70 raised off the weighing assembly 10, the microprocessor then displays a "LOAD SAMPLE" command on display window 28. Then, the operator loads a prepared sample between sample holder 48 and sample cover 50. Samples of fresh meat are prepared by grinding a sample through a conventional meat grinder and then mixing it to obtain a uniform composition. For best results, both the amount of mixing and temperature of the sample are controlled to enable accurate calibration of the analyzer and accurate sample analysis. It has been found that mixing for about 30 seconds at from 30°–50° F. produces satisfactory results.

After the operator closes the oven door 16 and touches the CONT switch 30, the microprocessor then performs a check to ascertain that the sample weight is within the desired range, for example 70 to 80 grams. First, the weight of the sample and sample holder assembly (denoted SAM and SPT) are taken and the initial sample weight calculation, SAM=(SAM+SPT)−SPT, is performed. If the sample weight should be above or below the desired range, the weight is displayed to the operator with the message "RELOAD". The operator is then required to adjust the sample weight to the proper range and again touch the CONT switch 30 to initiate the checking procedure. Once the sample weight is found to be within the proper range, the calculated weight value for the sample (SAM) is stored.

The operation for the analysis of a salted meat sample differs slightly from fresh meat analysis operation. This is due to the fact that meat proteins, as with many food proteins, have the ability to bind or encapsulate fat in an emulsion. The addition of salt to meat blends in meat processing operations aids in solubilizing the meat proteins and enables a greater amount of binding of fats. Likewise, temperature is an important factor in forming emulsions in a blended meat product, with higher temperatures (i.e., 50°–60° F.) producing more stable emulsions as opposed to lower temperatures (i.e., 30°–40° F.). Thus, varying the salt content, temperature, and amount of mixing of any meat blend varies the amount of fat bound in a meat sample of this blend and varies the resulting amount of fat rendered from a sample during heating. Accurate calibration becomes impossible for salted and blended samples which have undergone an indeterminate amount of mixing at an unknown temperature in the processing operation and during sample preparation. Thus, all sample preparations for a finished sample should be carried out for a definite time (i.e., 30 seconds to 1 minute) and at a temperature between 30° and 50° F.

In order to standardize the fat binding characteristics of salted blended meat samples, acid is added to the samples in an amount sufficient to lower the pH of the sample below the isoelectric point of the protein in the meat. At a pH below the isoelectric point, meat proteins have much less binding effect on fat and moisture, and the effects of the addition of salt to the meat can be counteracted.

It has been found that the use of citric acid for this purpose produces satisfactory results from the standpoint of ease of handling and production of samples from which accurate calibration measurements can be taken, although other acids may be utilized. A preferred form of citric acid is an encapsulated citric acid product commercially available from Durkee Foods, Inc. under the name Durkote citric acid (SR) (small, granular). For use in this invention, the encapsulated acid is packaged in the form of a pillow or capsule. The citric acid is encapsulated in a fatty material which melts at 145°–150° F. Thus, the citric acid product may be mixed with a meat sample and the desirable pH lowering effect of the acid taken advantage of during cooking of the sample. It has been found that the addition of about 3 grams of this acid product to a 70–80 gram sample of meat produces satisfactory results.

In operation, the appropriate meat type code (i.e., blend=2, blend with water=3) is entered and the microprocessor utilizes the proper calibrated constant values for the program commands and required calculations. In addition to entering the appropriate meat type code, run number, and sample temperature, the operator must input the percentage of salt (salt weight divided by meat weight) in the sample to be analyzed.

The operator then prepares the oven as described above. However, when the CONT switch 30 is touched, the display window 28 will indicate "PRE-LOAD SAMPLE" instead of "LOAD SAMPLE" as described above. As before, the operator places the prepared meat sample on the sample holder assembly and by touching the CONT switch causes the microprocessor to read the balance weight measurement, SAM+SPT, calculate the sample weight, SAM=(SAM+SPT)−SPT, and then check if the sample weight is within the required 70 to 80 gram range. If the sample is within the proper weight range, its weight value is stored and the display will change to indicate "LOAD SAMPLE & ACID". The operator responds by opening the oven door and removing the sample to a mixing bowl. The contents of an acid pillow is added to the meat sample and mixed. The acid pillow preferably contains citric acid which acts to aid in the release of fat and moisture during the subsequent cooking of the sample. After the acid is mixed with the meat sample, the sample is then placed between the sample holder 48 and cover 50 and all are loaded on the sample holder assembly 36. The door is closed and the CONT switch 30 touched.

The microprocessor then reads the combined balance weight measurement of the sample, sample holder assembly, and acid (denoted as SAM+SPT+ACD) and calculates the weight of the sample and acid, SAM+ACD=(SAM+SPT+ACD)−SPT. Following that step, the weight of the acid is calculated (ACD=(SAM+ACD)−SAM) and a comparison is made to determine if the value ACD is greater than 1 gram. If it is greater, then the value SAM+ACD is substituted in storage for the value SAM and will thus replace SAM in calculation of subsequent values by the microprocessor.

The remainder of the analysis process is followed for all meat type codes. The microprocessor now turns on the power to oven 12 and cooking of the sample is commenced. The command "IN PROCESS" is displayed in window 28 during cooking. The microprocessor continuously monitors the change in weight of the sample during cooking until the time rate of change of weight loss is less than a predetermined value. A technique for accurate determination of oven turn-off is taught in U.S. Pat. Nos. 3,890,825 and 3,916,670 incorporated herein by reference. Procedures analogous to those taught in these patents are also utilized in the present system.

However, the above-described process and apparatus improve upon the methods taught in the above patents to achieve even more accurate determinations. Because the rendered fat is collected in dish 70 which is raised off of weighing balance 10, erratic fluctuations in weight readings caused by spattering or dripping and explosions in the collected fat are avoided. Since the weight loss being monitored is the sum of vaporized moisture and rendered fat, larger values are being measured with less chance of erroneous readings. The addition of acid to salted and/or blended meat samples standardizes their characteristics for purposes of accurate sample calibration. Moreover, the use of a magnetic coupling of the stem and sample holder assembly to the weighing balance mechanism avoids possibly damaging forces and torques to the balance.

Once it has been ascertained by the microprocessor that the rate of sample weight decrease has declined to less than a predetermined value, the oven is turned off. After turn-off, dish 70 is lowered onto sample holder assembly 36 by activation of drive means 72. The total sample weight (denoted CTF) including the weight of the sample residue, fat, sample holder, sample holder cover, and holder assembly is then measured after a 10 second delay. This delay provides for the lapse of a period of time sufficient for spattering (or dripping) and explosions of rendered fat in the dish to have substantially subsided by the time the weight measurement is taken. After this delay, the microprocessor causes the caption "REMOVE RESIDUE" to be displayed. The operator then opens the oven door 16, removes the residue from the sample holder assembly, closes the door, and touches CONT switch 30 to cause the weight (denoted FNL) of the rendered fat, cover, holder, and holder assembly to be measured and stored. The microprocessor then automatically raises dish support assembly 52 with dish 70 off of the weighing balance in preparation for the next sample analysis.

Using the measured and stored weights, stored constants, derived weights, and the equations as defined below, the microprocessor can then calculate the percentages of fat, moisture, and protein in the sample. These final percentages (TPF, TPM, and TPP) are then displayed on window 28 and printed out by the printer 23 for a permanent record of the sample.

DEFINITIONS

| | | Definitions |
|---|---|---|
| SPT | = | Weight of sample holder and cover and sample holder assembly. |
| S&D | = | SPT plus weight of collection dish. |
| DSH | = | S&D − SPT, weight of collection dish including watchglass and paper. |
| SAM | = | Initial weight of sample. |
| ACD | = | Weight of acid. |
| CTF | = | Weight at cut-off of cooking of sample residue and rendered fat plus sample holder and cover, sample holder assembly, and collection dish. |
| FAT | = | Weight of rendered fat. |
| MST | = | Weight of vaporized moisture. |

-continued

| | | Definitions |
|---|---|---|
| RES | = | Weight of sample residue. |
| FNL | = | Weight of rendered fat plus sample holder and cover, sample holder assembly, and collection dish. |
| RPF | = | Raw percent fat or fat percent by weight. |
| RPM | = | Raw percent moisture or moisture percent by weight. |
| TPF | = | True percent fat-correlated value. |
| TPM | = | True percent moisture-correlated value. |
| TPP | = | True percent protein-correlated value. |

EQUATIONS

| | | Equations |
|---|---|---|
| DSH | = | S&D − SPT |
| SAM | = | (SAM + SPT) − SPT |
| SAM | & | ACD = (SAM + SPT + ACD) − SPT |
| ACD | = | (SAM + ACD) − SAM |
| CTF | = | S&D + SAM − MST |
| FNL | = | S&D + FAT |
| FAT | = | FNL − S&D |
| MST | = | S&D + SAM − CTF |
| RPF | = | FAT/SAM |
| RPM | = | MST/SAM |
| TPF | = | $K_0 \pm K_1(RPF) \pm K_2(RPM) \pm K_3(TEMP) \pm K_4(SALT)$ |
| TPM | = | $K_0 \pm K_1(RPF) \pm K_2(RPM) \pm K_3(TEMP) \pm K_4(SALT)$ |
| TPP | = | $K_{1p} - K_{2p}(TPF) - TPM - SALT\%$ |

While the methods and apparatus described herein constitute preferred embodiments of the invention, it is to be understood that the invention is not limited to these precise methods and apparatus, and that changes may be made without departing from the scope of the invention, which is defined in the appended claims.

What is claimed is:

1. In a method of determining the amount of fat in a sample of a salted meat wherein the fat is heat releasable in liquid form from the sample, said method including the steps of (a) applying energy to said sample to heat the same and cause fat in said sample to be rendered as a liquid, (b) continuously monitoring the weight of said sample during the applying of energy thereto at least from a time when said sample begins losing weight, and (c) terminating the applying of energy to said sample once the residue of said sample reaches a predetermined chemical consistency, the improvement comprising:

preparatory to applying energy to said sample, mixing with said sample an amount of acid sufficient to lower the pH of the sample to below the isoelectric point of the protein contained therein.

2. The method of claim 1 in which the acid is citric acid.

3. The method of claim 2 in which the citric acid is encapsulated and the encapsulating material melts away during the application of energy to the sample.

4. The method of claim 1 in which the mixing is carried out for about 30 seconds and the temperature of the sample is maintained between about 30° and 50° F.

5. In a method of determining the amount of fat, moisture, and/or protein in a salted meat product sample, said method including the steps of (a) locating said salted meat product sample on a weighing balance, (b) weighing said sample, (c) applying energy to said sample to heat the same and cause fat in said sample to be released as a liquid and moisture in said sample to be released as a vapor, (d) continuously monitoring the weight of said sample during the applying of energy thereto at least from a time when said sample begins losing weight, and (e) terminating the applying of energy to said sample when the time rate of change of the weight of said sample reaches a predetermined rate, the improvement comprising:

preparatory to applying energy to said sample, mixing with said sample an amount of acid sufficient to lower the pH of the sample to below the isoelectric point of the protein contained therein, and re-weighing the combined acid plus sample.

6. The method of claim 5 in which the acid is citric acid.

7. The method of claim 6 in which the citric acid is encapsulated and the encapsulating material melts away during the application of energy to the sample.

8. The method of claim 5 in which the mixing is carried out for about 30 seconds and the temperature of the sample is maintained between about 30° and 50° F.

* * * * *